(12) United States Patent
Picardo et al.

(10) Patent No.: US 7,016,726 B1
(45) Date of Patent: Mar. 21, 2006

(54) SMART MEDICAL CONNECTOR SYSTEM AND METHOD OF USE

(75) Inventors: Anthony G. Picardo, Tacoma, WA (US); Thomas Allen Solosko, Issaquah, WA (US); Joseph R. Diederichs, Seattle, WA (US); Kim J. Hansen, Renton, WA (US); Christine Janae, Seattle, WA (US); Paul I. Szabo, Seattle, WA (US); John A. Moren, Edmonds, WA (US); Ian G. MacDuff, Bothell, WA (US); Steven W. Ranta, Seattle, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/574,688

(22) Filed: May 17, 2000

(51) Int. Cl.
*A61N 1/18* (2006.01)

(52) U.S. Cl. .................. 607/5; 607/7; 607/63; 439/488; 239/449

(58) Field of Classification Search .................. 607/2, 607/5–6, 37, 63, 115, 119, 38, 7; 439/955, 439/488–491; 239/449–450
See application file for complete search history.

(56) References Cited

U.S. PATENT DOCUMENTS

| | | | | |
|---|---|---|---|---|
| 4,811,002 A | * | 3/1989 | Otsubo | 340/687 |
| 4,834,103 A | * | 5/1989 | Heath | 600/372 |
| 4,902,244 A | * | 2/1990 | Endo et al. | 439/489 |
| 5,222,164 A | * | 6/1993 | Bass et al. | 385/14 |
| 5,284,135 A | * | 2/1994 | Lopin | 607/4 |
| 5,441,520 A | * | 8/1995 | Olsen et al. | 607/115 |
| 5,588,873 A | * | 12/1996 | Hamai et al. | 439/489 |
| 5,607,454 A | | 3/1997 | Cameron et al. | |
| 5,660,567 A | * | 8/1997 | Nierlich et al. | 439/620 |
| 5,713,927 A | * | 2/1998 | Hampele et al. | 607/5 |
| 5,735,879 A | | 4/1998 | Gliner et al. | |
| 5,836,993 A | | 11/1998 | Cole | |
| 5,879,374 A | | 3/1999 | Powers et al. | |
| 5,967,817 A | | 10/1999 | Greenstein | |
| 6,334,070 B1 | * | 12/2001 | Nova et al. | 607/5 |
| 6,360,120 B1 | * | 3/2002 | Powers et al. | 600/510 |

OTHER PUBLICATIONS

Cummins, et al., Improving Survival From Sudden Cardiac Arrest: The "Chain of Survival" Concept *Circulation* 83(5): 1832-1847 (1991).
The Critical Moment, Newman et al, Early Defibrillation Making Waves Across America JEMS Supplement, S4-S8 (Jan. 1997).

* cited by examiner

Primary Examiner—Mark Bockelman
(74) *Attorney, Agent, or Firm*—Tony Piotrowski

(57) ABSTRACT

A method and apparatus for identifying electrodes attached to a defibrillator and adjusting patient therapy delivered by a defibrillator in response thereto.

19 Claims, 5 Drawing Sheets

SMART MEDICAL CONNECTOR SYSTEM AND METHOD OF USE

BACKGROUND OF THE INVENTION

1. Field of the Invention

This invention relates generally to a method and apparatus for identifying electrodes attached to a defibrillator. In particular, this invention relates to providing an identification module within the electrode connector. The electrotherapy device identifies the electrodes attached to the patient based on the identification module and adjusts defibrillator operation based upon the identification. Electrotherapy devices include defibrillators, cardioverters and training devices that simulate the operation of an electrotherapy device. Defibrillators include automatic or semi-automatic external defibrillators (AEDs).

2. Description of the Prior Art

Electrotherapy devices are used to provide electric shocks to treat patients for a variety of heart arrhythmias. For example, external defibrillators typically provide relatively high-energy shocks to a patient (as compared to implantable defibrillators), usually through electrodes attached to the patient's torso. External defibrillators are used to convert ventricular fibrillation or shockable tachycardia to a normal sinus rhythm. Similarly, external cardioverters can be used to provide paced shocks to convert atrial fibrillation to a more normal heart rhythm.

In 1991 the Advanced Cardiac Life Support Subcommittee of the American Heart Associate made a report to Health Professionals calling for increased access to defibrillation in order to improve the survival rates from sudden cardiac arrest (SCA). [Cummins, et al. "Improving Survival From Sudden Cardiac Arrest: The 'Chain of Survival' Concept" Circulation 83(5): 1832–1847 (1991).] The statistics themselves are staggering. On average 1000 adults die from SCA each day. Over 70% of these deaths occur in the home. Because the survival rate decreases 10% for every minute that passes, unless a defibrillator is available within the first few critical minutes, a victim of SCA has little chance of survival. If defibrillation were available, many of these people would survive. Following the AHA's recommendations, there has been increased awareness of the importance of public access defibrillation and defibrillators have become increasingly available. [See, e.g., Newman, "Early Defibrillation—Making Waves Across America," JEMS Suppl. S4–S8 (January 1997).] The first phase of early defibrillation has been training designated lay responders in proper deployment of a defibrillator. Designated lay responders include, for example, fire fighters, police officers, flight attendants and security guards. However, with 70% of SCA occurring in the home, it becomes increasingly important to design a device that can be deployed by the average citizen in a home emergency.

One problem that could arise as defibrillators become ubiquitous relates to the ability to modify defibrillator operation based on the patient, e.g. infant, pediatric or adult. Currently, AEDs operate according to a single protocol for all patients and are generally not configured for use on children under 8 (the definition of pediatric patients according to the American Heart Association). As more information becomes available about the incidence of SCA in pediatric patients, it will likely be important to provide a mechanism to defibrillator a pediatric patient that is uncomplicated.

What is needed is a method and apparatus for identifying the electrodes to the defibrillator.

SUMMARY OF THE INVENTION

An electrical medical electrode connector is provided. The electrical medical electrode connector comprises: a housing, wherein at least one end of the housing forms a cable connector; an electrical conductor electrically connected to a socket within a shell of the cable connector; and an identifier disposed within the housing that communicates information to a defibrillator. A pair of defibrillator electrodes may be electrically connected to the housing. Alternatively, a set of monitoring pads electrically connected to the housing. In either case, the medical electrode is typically comprised of a plurality of electrode pads. For the monitoring scenario, a preferred embodiment incorporates three electrode pads, five electrode pads or twelve electrode pads. The identifier communicates an identification value from the medical electrode. The communication values can be those corresponding to: light amplitude, wavelength, polarization, hertz, resistance, capacitance, gauss, electrical contact. The identifier may be optical, electromechanical, electrical, resistive, capacitive, or magnetic.

A defibrillator system is also provided. The defibrillator system comprises: at least one electrode pad having an electrode pad type operable to contact a patient; a medical electrode connector, connected to the defibrillator electrode pad on one end and the defibrillator on the other end, operable to identify the electrode pad type to the defibrillator; a front-end circuit operation to be coupled to the electrode pad and to receive identification information from the electrode pad; a shock delivery circuit coupled to the electrode pad; and a processor coupled to the front-end and shock delivery circuits and operable to determine whether the patient is experiencing a shockable heart condition and to enable the shock-delivery circuit to deliver a shock to the patient via the electrode pads if the processor determines that the patient is experiencing a shockable heart condition. The medical electrode connector is removably connectable to the defibrillator. The defibrillator of claim 10 wherein the medical electrode connector is removably connectable to the electrode pads. The medical electrode connector has an identification module operation identify the electrode pad type to the defibrillator. The identification module communications at least one identification value to the defibrillator. The identification value can be any of light, open/short, resonant frequency, resistance, capacitance, or gauss. An identifier receiver operable to interface between the medical electrode connector and the front-end circuit may also be provided.

A method of deploying a defibrillator is also contemplated. The method comprises: turning the defibrillator on; attaching electrode pads to a patient; inserting a cable connector associated with the electrode pads into a housing for receiving the cable connector within the defibrillator; identifying the type of electrode pads based on an identifier within the cable connector associated with the electrode pads; altering therapy delivered by the defibrillator based on the type of electrode pads identified; and altering patient care instructions such as CPR based on the type of electrode pads identified. Additionally, the amount of energy delivered to a patient in response to the electrode pad identification may be adjusted. Applicant also contemplates lowering the amount of energy delivered to a patient if the electrodes are identified as infant electrodes or child electrodes. Otherwise, the defibrillator will follow a default therapy protocol if the electrode identification value is not recognized or if no electrode identification value is received. A patient treatment protocol, such as CPR, may also be altered to conform to the type of patient being treated in response to the identification. In that case, the protocol would be changed to the infant CPR protocol if the electrodes are identified as infant electrodes, child CPR protocol if the electrodes are identified as child electrodes, a default CPR protocol if the electrode identification value is not recognized or if no electrode identification value is received. The CPR protocol may be the CPR protocol recommended by the American Heart Association if the electrodes are identified as AHA electrodes or the CPR protocol recommended by the European Resuscitation Council if the electrodes are identified as ERC electrodes. Thus, the method includes indicating use of the CPR protocol recommended by specific organizations if the electrodes are identified as electrodes specific to that organization.

BRIEF DESCRIPTION OF THE DRAWINGS

In FIG. 1, the electrode system 36 includes an identification module or identifier 32, an electrode adapter 26 and electrodes 28.

DESCRIPTION OF THE PREFERRED EMBODIMENTS

The following discussion is presented to enable a person skilled in the art to make and use the invention. Various modifications to the preferred embodiment will be readily apparent to those skilled in the art, and the generic principles herein may be applied to other embodiments and applications without departing from the spirit and scope of the present invention as defined by the appended claims. Thus, the present invention is not intended to be limited to the embodiment show, but is to be accorded the widest scope consistent with the principles and features disclosed herein.

Figure 1:
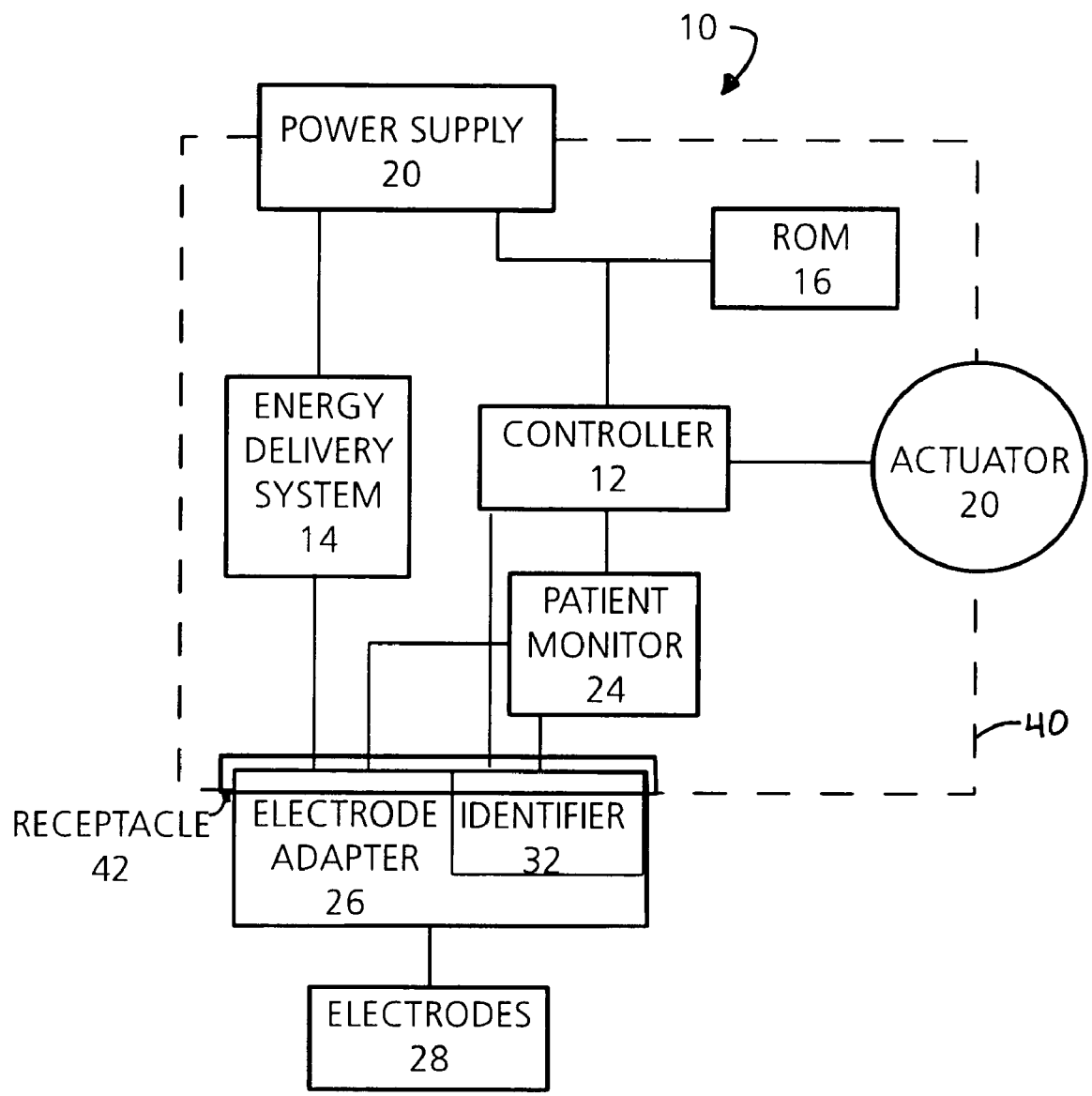
FIG. 1 is a block diagram of an electrotherapy device showing a detachable electrode system.

FIG. 1 is a block diagram showing a device 10. Device 10 is an electrotherapy device. The device 10 may include the ability to defibrillate, cardiovert, or pace a patient, or a combination of these features. Device 10 has a controller 12 that operates an energy delivery system 14 and performs other aspects of the operation of the device. Software instructions for the operation of the device are accessible from read only memory (ROM), such as incorporated ROM 16. The controller accesses instructions for operation from ROM 16. It should be understood that, in this and other embodiments described below, "controller" means a microprocessor, controller, gate array, other control logic, or any combination of these elements. The device components are typically located within a device housing 40. The device housing 40 has receptacle 42 for receiving an electrode connector 26.

As contemplated by this embodiment, an identification module 32 is integral with the electrode connector 26. The electrode connector 26 is connected to electrodes 28, the whole assembly being removably connected to the receptacle 42 in device housing 40. The identification module 32 in the adapter 26 uniquely identifies the electrode connector 26 to the defibrillator. Thus, identifying the type of electrodes attached to the defibrillator. A suitable electrode system 36 to be adapted for use in this invention would be, for example, Heartstream ForeRunner® electrodes.

Once the electrode connector 26 is attached to the device 10, identification module 32 communicates with controller 12. Communication with the controller 12 may be direct or through an identifier receiver (not shown) which interfaces between the controller 12 and the identifier 32.

Electrodes 28 communicate with a patient monitor 24 via the electrode connector 26 attached to the device 10 through receptacle 42. Electrodes 28 provide patient ECG data from the patient to the patient monitor 24. Electrodes include electrodes capable of delivering defibrillation, monitoring a patient condition, delivering pacing pulses, or a combination of those features. In an AED, the patient monitor 24 monitors the patient for a heart rhythm and subsequently determines whether the monitored rhythm is shockable. When the rhythm is shockable, the patient monitor 24 then communicates a shock decision to the controller 12. The controller 12, then communicates to the energy delivery system 14. The energy delivery system 14, then delivers a therapeutic energy pulse to the patient (not shown) through electrodes 28 attached to the defibrillator 10 via electrode connector 26, using the power supply 20 as the energy source. As will be appreciated by those of skill in the art, the identification module 32 may be any of a number of solutions, discussed in more detail below.

In one embodiment, an optical encoding solution is contemplated. In this scenario, a light source is provided in view of a photosensitive light receiver in the body of the defibrillator near to or part of the electrode connector 26. Integrated into the electrode connector 26 are devices that will alter the characteristics of the light as received by the photosensor. In a simple embodiment the characteristic would be detection of the presence or absence of one or more windows in the connector body by detecting the presence or absence of light impinging upon the photosensor. In this case, the light source and photosensor would be arranged such that they straddle the electrode connector receptacle. As one skilled in the art can appreciate, a plurality of windows would permit encoding of the type of electrode attached to the connector. A more sophisticated approach would use a window or windows of varying optical density or color which would vary the amplitude or wavelength of the received light. The use of windows of varying optical density increases the efficiency of the electrode encoding scheme—allowing more electrode types or the use of fewer windows.

Using a simple "on/off" embodiment with two "windows" as an example, electrodes intended for use on an infant patient could be identified by having one of the windows transmissive and the other opaque, electrodes for pediatric use could have one window transmissive and the other opaque (opposite of the case for the infant patient), and electrodes for adult use would have both windows opaque. The situation where light is received by both photodetectors could be reserved for self test of the system when no electrode connector is inserted. Thus, if neither of the two photodetectors receives light, the defibrillator identifies the electrodes as being those for use on an adult and follows the adult therapy protocol and energy delivery behavior. While this particular embodiment utilizes the transmissive qualities of light, it can be appreciated by those skilled in the art that other techniques to modify the characteristics of light such as reflection, polarization, absorption, refraction, or diffraction can be used successfully as well.

In yet another embodiment, electromechanical encoding may be provided. In that case interface electronics within the defibrillator such as switches or other means to make or break electrical contact would be activated by mechanical protrusions or depressions in the electrode connector body. Persons skilled in the art can envision several encoding schemes ranging from simple binary (switch open/closed) forms to mechanical barcode equivalents consisting of complex open and closing sequences as the connector is inserted into the electrode connector receptacle. Furthermore, it can be appreciated that switch actuation may be due to other forces such as magnetic or proximity.

In yet another embodiment, electrical contact encoding may be provided. In that case, interface electronics in the defibrillator sense the presence or absence of direct electrical connections between various contacts in the connector socket engaged by mating contacts in a particular connector. The interface electronics could comprise digital electronic inputs resistively pulled up to a power supply, with the connector contacts arranged to pull down the inputs thereby facilitating sensing by a circuit such as a logic element or a comparator. A plurality of contacts could be used in various combinations to indicate one from among a set of possible combinations. For example, with three possible connections to a fourth common connection, the presence of all three connections identifies the electrodes as being those for use on an adult and follows the adult therapy protocol and energy delivery behavior. The connection set could be further extended to implement error detection and/or correction if needed to mitigate hazards that might exist.

In yet another embodiment, RF encoding may be provided. In that case, an RF transmitter and RF receiver are provided in the defibrillator in the vicinity of the connector socket. The connector of this embodiment would have specific resonant electrical characteristics determined by indwelling inductive and capacitive circuit elements that identify the electrode type. The resonant properties of the connector modify the RF signal sent from the RF transmitter to the RF receiver in such a way as to change its amplitude at the receiver as a function of frequency. For example, electrodes intended for use on an infant patient could be identified as having the received signal amplitude at a maximum at 100 kHz, pediatric electrodes at 200 kHz, and adult electrodes at 400 kHz. Thus, for example when a peak frequency of 400 kHz is detected, the defibrillator identifies the electrodes as being those for use on an adult and follows the adult therapy protocol and energy delivery behavior.

In yet another embodiment, resistance encoding may be provided. In that case, a connector with specific resistance across sense connections is provided. The defibrillator forms a voltage divider from a reference voltage between a reference resistance and the variable connector resistance and measures the divided voltage with an A/D converter to determine the type of connector installed. For example, electrodes intended for use on an infant patient could be identified as 1000 Ohms, pediatric electrodes as 2000 Ohms, and adult electrodes as 3000 Ohms. The defibrillator could use a 10000 Ohm reference resistance, in which case an A/D converter reading corresponding to 23% of the reference voltage would indicate the presence of adult electrodes. The defibrillator would then follow adult therapy protocol and energy delivery behavior.

In yet another embodiment, capacitance encoding may be provided. In that case, a connector with specific capacitance across sense connections is provided. The defibrillator may apply a reference voltage to the connector capacitor, and then discharge the connector capacitor into a reference resistance, sensing with a comparator when the voltage has decayed to 37% of the reference. Measuring this decay time with a timer could then be used to determine the type of connector installed. For example, electrodes intended for use on an infant patient could be identified as 0.1 $\mu$F, pediatric electrodes as 0.2° F., and adult electrodes as 0.3 $\mu$F. The defibrillator could use a 10000 Ohm reference resistance, in which case a decay time of 3 ms would indicate the presence of adult electrodes. The defibrillator would then follow adult therapy protocol and energy delivery behavior.

In yet another embodiment, magnetic encoding may be provided. In that case, a connector containing one or more magnets with a specific magnetic field may be provided. Based on the strength of the magnetic field, the controller 12 adjusts its operation to correspond to the identification. For example, electrodes intended for use on an infant patient could be identified as containing 2 magnets, pediatric electrodes contain 1 magnet, and adult electrodes none. Thus, for example when the detected magnetic field falls below the minimum threshold, the defibrillator identifies the electrodes as being those for use on an adult and follows the adult protocol and energy delivery behavior. As will be appreciated by those skilled in the art, the encoding scheme could employ the orientation of the field or the physical location within the electrode connector body of the detected field.

Further, it will be appreciated by those in skill of the art, that other adjustments to operational behavior could be followed without departing from the scope of the invention.

Figure 2A:
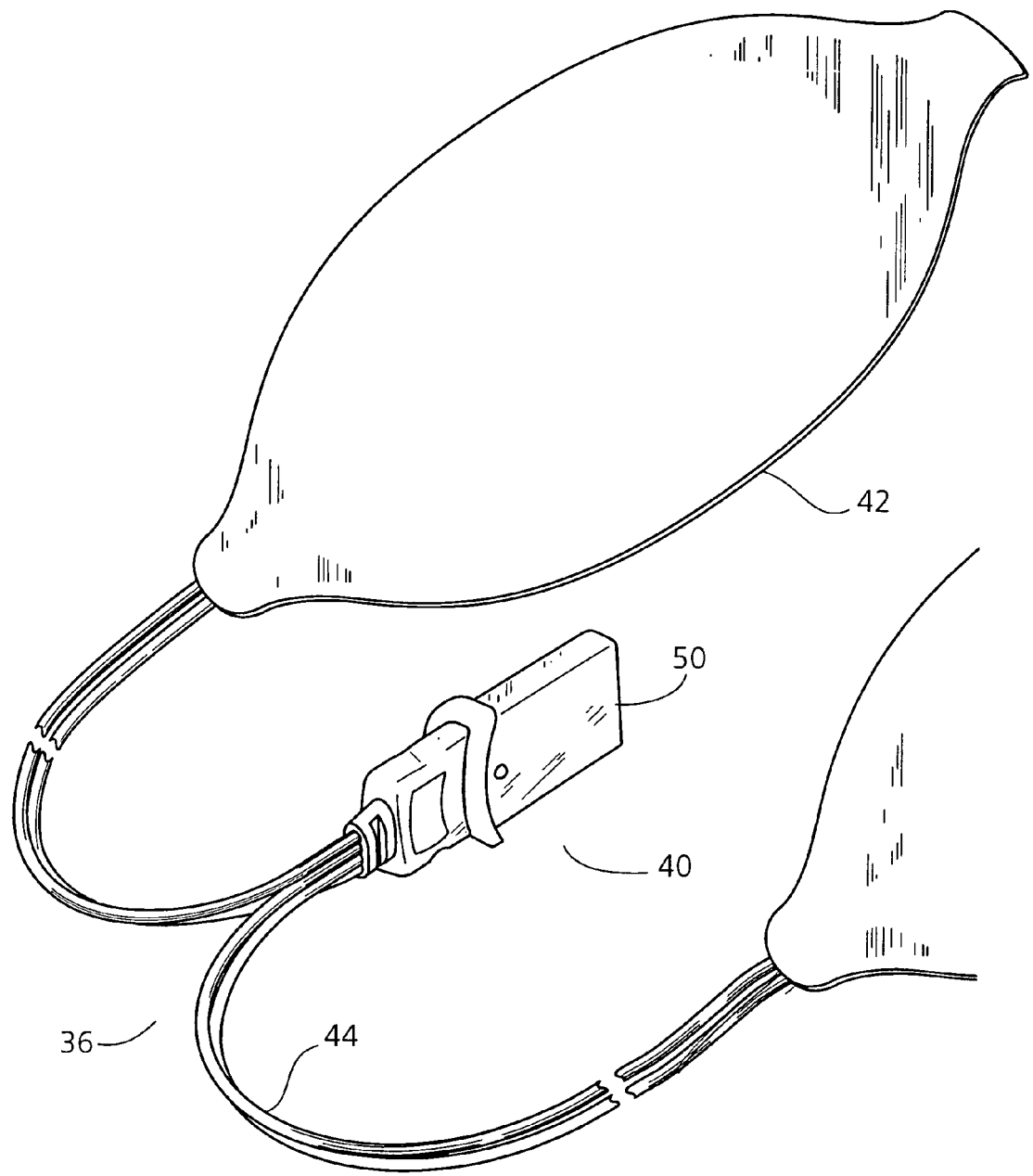
FIG. 2a is a perspective drawing of an electrode system comprising a pair of disposable electrodes integrally formed with an electrode connector that includes features that identify the type of disposable electrodes attached to the connector.

Turning to FIG. 2a, electrode system 36 comprises an electrode connector housing 40 for connecting the electrode system 36 to device (not shown). In this embodiment, the housing 40 comprises a cable connector 50. The cable connector 50 has one or more electrical conductors electrically connected to corresponding sockets within a shell. A pair of electrodes 42 are connected to the housing 40 via wires 44. For purposes of illustration, FIG. 2a has been depicted showing two electrodes. However, it will be appreciated by those of skill in the art that a plurality of electrodes can be used. For example, from 2–12 electrodes are appropriate for use in monitoring patient ECG. Additional information on electrode connector construction can be found in U.S. Pat. No. 5,967,817 by Greenstein entitled "Medical Connector Apparatus," the disclosure of which is incorporated herein.

Figure 2B:
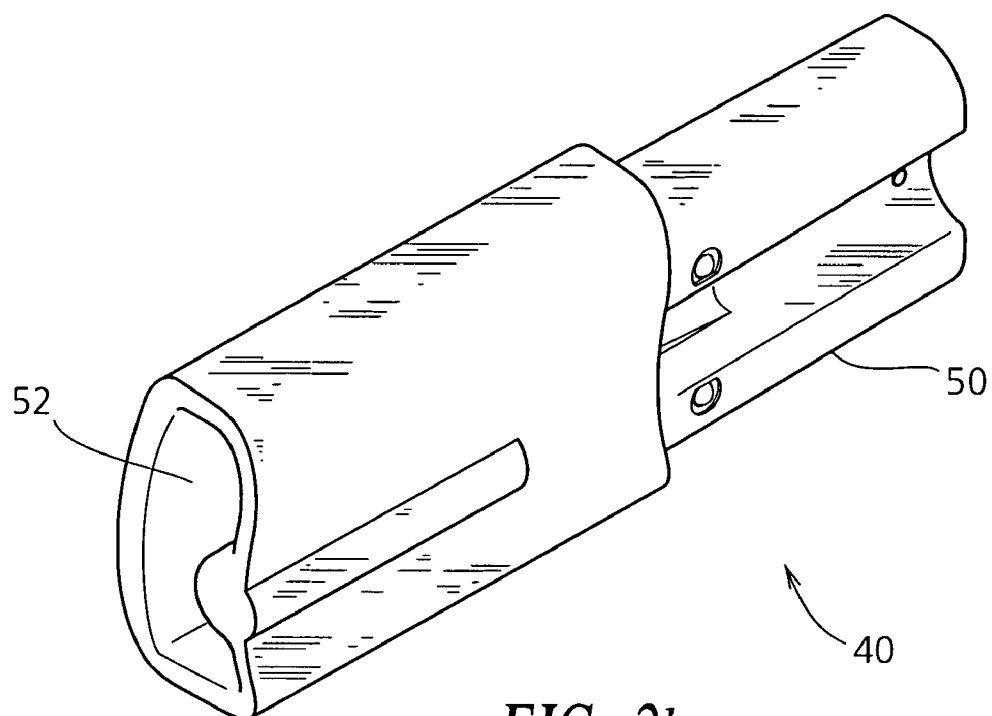
FIG. 2b is a perspective drawing of an electrode connector receptacle in the form of an adapter having an identification module for use in connection with a defibrillator and a pair of disposable electrodes.

Turning now to FIG. 2b, the housing 40 of the electrode connector receptacle shown in FIG. 2a has been modified so that in addition to providing a cable connector 50, it also is adapted to receive a mating cable connector on one end. Thus, one end forms an interior chamber 52 for receiving a mating cable connector. Electrical conductors electrically connected to sockets within a shell are located within the interior chamber 52 such then when a mating cable connector is inserted into the interior chamber of the receptacle it makes electrical contact between the mating cable connector and housing 40. In this embodiment, the receptacle is configured so that it is removable from the electrode pads and the defibrillator and thus is reusable.

Figure 2C:
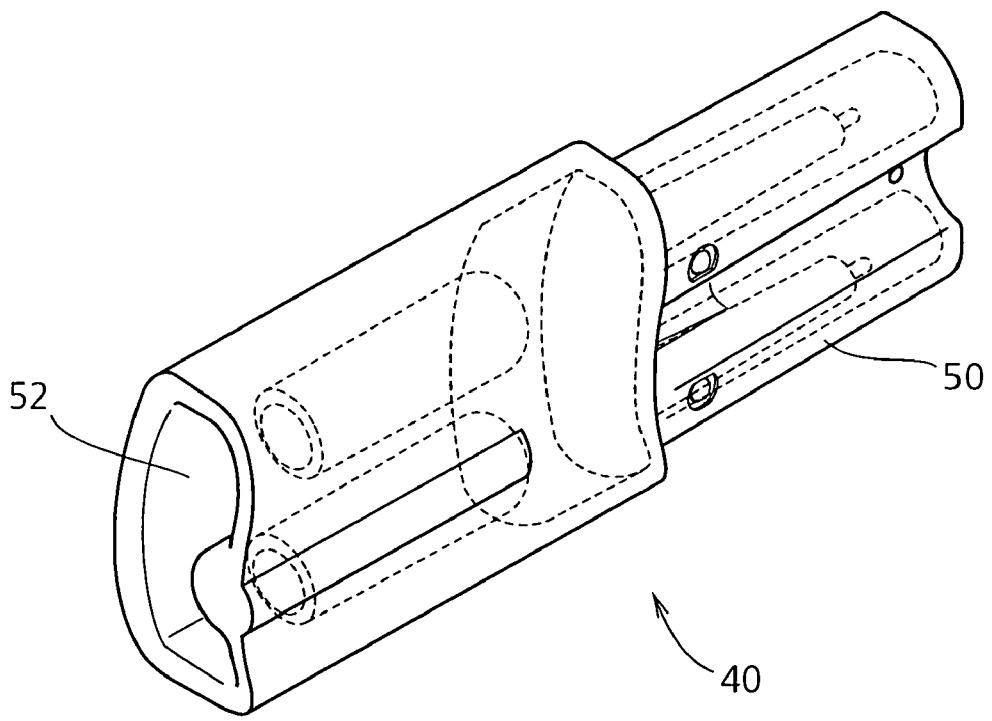
FIG. 2c is a perspective drawing of an electrode connector receptacle in the form of an adapter having an identification module for use in connection with a defibrillator and a pair of disposable electrodes showing the interior portions of the male and female ends of the adapter.

FIG. 2c illustrates the adapter set-up shown in FIG. 2b with the interior portions outlined. As illustrated, the interior female chamber 52 houses two connectors with female chambers. The connectors are adapted to slide over male conductors in a corresponding electrode adapter. The male cable connector end 52 has two female chambers each of which contains a male conductor. When the male cable connector end 52 is inserted into a corresponding female chamber (for example, in a defibrillator housing), the male cable connector slides into the female connector, while the two connectors with female chambers slide over the male conductors of the male cable connector.

As will be appreciated by those of skill in the art, the form factors shown in FIGS. 2a–2c are provided for illustration only. Other form factors may be used without departing from the scope of the invention.

Figure 3:
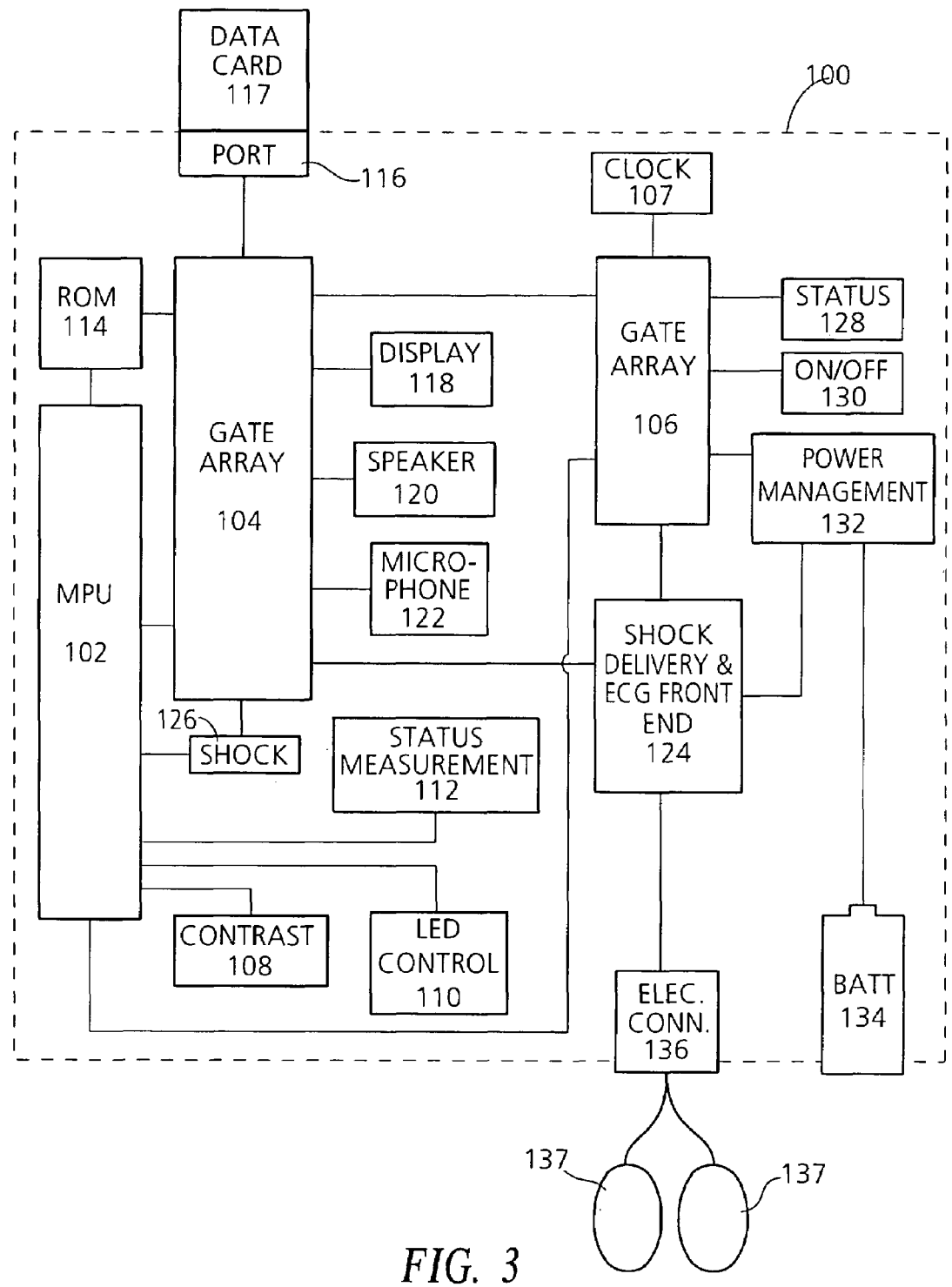
FIG. 3 shows the major components of a semi-automatic external defibrillator in block diagram form.

The major components of an AED are shown in FIG. 3 in block diagram form.

Further detailed information about the operation of an AED can be obtained in U.S. Pat. No. 5,836,993, to Cole for "Electrotherapy Device Control System and Method," the specification of which is incorporated herein. As will be appreciated by those of skill in the art, the invention can be used in a variety of AEDs and is not limited to this configuration, which is used for illustration purposes only.

In this illustration, defibrillator control functions are divided among a microprocessor unit (MPU) 102 and two custom gate arrays 104 and 106.

MPU 102 performs program steps according to software instructions provided to it from ROM 114. MPU 102 controls the operation of certain buttons (such as display contrast buttons 108) and certain system LED's 110 (such as LED's associated with the shock button and the electrode connector). MPU 102 also receives system status information as shown by block 112.

Gate array 104 implements the memory map to system ROM 114. System ROM 114 is preferably flash ROM, although EPROM or any other electrically erasable and programmable nonvolatile memory could be used. Gate array 104 also controls a display 118, a speaker 120, and a microphone 122. Gate array 104 can actuate a relay within the shock delivery and ECG front-end system 124 in response to actuation of a shock button 126 by a user during treatment mode.

Gate array 106 provides a system monitor function by performing automatic self-tests of the defibrillator and its components. The gate array 106 displays the operational status of the defibrillator on a status display 128. Details of suitable self-tests may be found in U.S. Pat. No. 5,879,374, to Powers, et al. for "External Defibrillator with Automated Self-Testing Prior to Use," the specification of which is incorporated herein by reference. Gate array 106 is also the defibrillator's interface with a user-activated on/off switch 130. Gate array 106 controls the power management subsystem 132 to provide power to operate system components from power supply 134 and to provide energy to the shock delivery system's capacitor(s) for a therapeutic shock during treatment mode. Gate array 106 also interfaces with the defibrillator's ECG front end, enables the shock delivery system to deliver a shock in response to detection of a patient ECG pattern requiring treatment (and actuation of the shock button), and controls delivery of the shock to electrode connector 136 in response to shock delivery status information obtained during delivery of the shock. Further information regarding this last function may be found in U.S. Pat. No. 5,735,879 to Gliner et al. for "Electrotherapy Method for External Defibrillators," and U.S. Pat. No. 5,607,454, to Cameron et al. for "Electrotherapy Method and Apparatus," the specifications of which are incorporated herein.

As described previously, electrical connector 136 may communicate directly with MPU 102 to identify the electrode type, or electrical connector 136 may communicate with MPU 102 via an identifier receiver that interfaces between the MPU 102 and the identifier of the electrical connector 136. For example, in the optical encoding solution, the photodetectors could act as an identifier receiver in communication between the MPU 102 and the electrical connector 136.

These defibrillator components communicate with each other over suitable communication buses, as shown.

External defibrillator 100 can be operated in different modes, such as self-test mode, stand-by mode, set-up mode, patient treatment mode, training mode and code-transfer mode. The operational characteristics of defibrillator 100 differ in each mode. In addition, the operational characteristics of the defibrillator in any one of the modes can be changed as explained below.

As is known in the art, while in patient treatment mode, the defibrillator 100 typically (1) determines whether electrodes 137 are attached to electrode connector 136; (2) receives ECG information from a patient through such electrodes; (3) analyzes the ECG information to determine whether a therapeutic shock is advised; and (4) delivers a shock to the patient through the electrodes 137 if a shock is advised and if the shock button 126 is actuated by a user.

Figure 4:
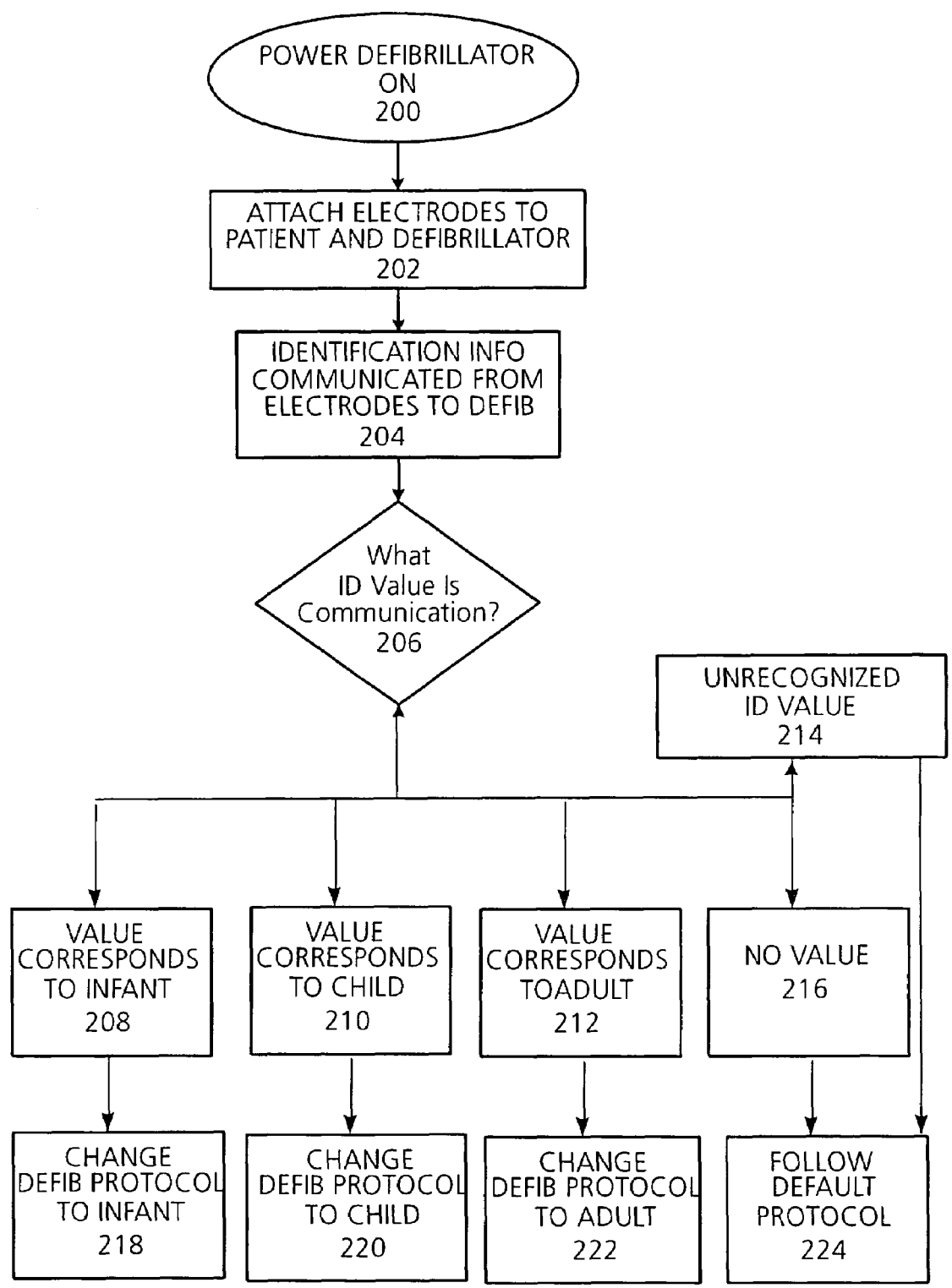
FIG. 4 is a flow chart showing the method of operating the electrotherapy device according to the invention.

Turning to FIG. 4, the method of deploying the invention is shown. Initially, the first responder defibrillator is powered up 200. Typically, but not necessarily, after powering the defibrillator, electrode pads are attached to the patient 202 and the electrode pads are connected to the defibrillator. The defibrillator then obtains value information from the attached electrode connector via its connector identification system 204. The defibrillator then determines the information communicated for the identification from the adapter 206. As discussed above, appropriate identification values include, for example: presence or absence of light, when the optical encoding scheme is employed; the state of electrical switches or contacts (open/short) when the electromechanical scheme is employed; resonant frequency characteristics when the RF encoding scheme is employed; resistance when the resistance encoding scheme is employed; capacitance, when the capacitance encoding scheme is employed; gauss, when the magnetic encoding scheme is employed; or any combination thereof.

If the value communicated corresponds to the value assigned for an infant patient 208, then the defibrillator follows a therapy protocol that is appropriate for an infant 218. If the value communicated corresponds to the value assigned for a child under the age of 8 210, then the defibrillator follows a therapy protocol that is appropriate for a child 220. If the value communicated corresponds to the value assigned for an adult patient 212, then the defibrillator follows a therapy protocol that is appropriate for an adult 222. If the value communicated does not correspond to a recognized value 214, or no value is communicated 214, then the defibrillator follows a default therapy protocol 224. Typically, the default protocol 224 is the protocol followed for delivering therapy to an adult patient 222.

As discussed above, other modifications falling within the scope of this invention will be apparent to persons of skill in the art. Thus, the invention is not to be limited by the specification, but interpreted according to claims that follow.

What is claimed is:

1. A defibrillator comprising:
   at least one electrode pad having an electrode pad type operable to contact a patient;
   a medical electrode connector, connected to the defibrillator electrode pad on one end and the defibrillator on the other end, and including a magnet which is operable to identify the electrode pad type to the defibrillator;
   a front-end circuit operation to be coupled to the electrode pad and to receive identification information from the electrode pad;
   a shock delivery circuit coupled to the electrode pad; and
   a processor coupled to the front-end and shock delivery circuits and operable to determine whether the patient is experiencing a shockable heart condition and to enable the shock-delivery circuit to deliver a shock to the patient via the electrode pads if the processor determines that the patient is experiencing a shockable heart condition,
   wherein the defibrillator further comprises means for detecting the magnetic field produced by the magnet when the medical electrode connector is connected to the defibrillator to identify the electrode pad type to the defibrillator.

2. The defibrillator of claim 1 wherein the medical electrode connector is removably connectable to the defibrillator.

3. The defibrillator of claim 1 wherein the means for sensing further comprises means for sensing the number of magnets in the medical electrode connector.

4. The defibrillator of claim 1 wherein the medical electrode connector has a plurality of magnets to identify the electrode pad type to the defibrillator.

5. A method of deploying a defibrillator comprising:
   tuning the defibrillator on;
   attaching electrode pads to a patient;
   inserting a cable connector containing a magnet which is associated with the electrode pads into a housing for receiving the cable connector within the defibrillator;
   identifying the type of electrode pads based on the magnet within the cable connector associated with the electrode pads, wherein said identifying step further comprises the step of detecting the magnetic field of the magnet within the defibrillator; and
   altering therapy delivered by the defibrillator based on the type of electrode pads identified.

6. The method of claim 5 further comprising the step of: adjusting the amount of energy delivered to a patient in response to the electrode pad identification.

7. The method of claim 5 further comprising the step of: lowering the amount of energy delivered to a patient if the electrodes are identified as infant electrodes.

8. The method of claim 5 further comprising the step of: lowering the amount of energy delivered to a patient if the electrodes are identified as child electrodes.

9. The method of claim 5 further comprising the step of: following a default therapy protocol if the electrode identification is not recognized.

10. The method of claim 5 further comprising the step of: following a default therapy protocol if no electrode identification is recognized.

11. The method of claim 5 further comprising the step of: altering a CPR patient treatment protocol to conform to the type of patient being treated.

12. The method of claim 5 further comprising the step of: indicating use of the infant CPR protocol if the electrodes are identified as infant electrodes.

13. The method of claim 5 further comprising the step of: indicating use of the child CPR protocol if the electrodes are identified as child electrodes.

14. The method of claim 5 further comprising the step of: following a default CPR protocol if the electrode identification is not recognized.

15. The method of claim 5 further comprising the step of: following a default CPR protocol if no electrode identification recognized.

16. The method of claim 5 further comprising the step of: indicating use of the CPR protocol recommended by the American Heart Association if the electrodes are identified as AHA electrodes.

17. The method of claim 5 further comprising the step of: indicating use of the CPR protocol recommended by the European Resuscitation Council if the electrodes are identified as ERC electrodes.

18. The method of claim 5 further comprising the step of: indicating use of the CPR protocol recommended by specific organizations if the electrodes are identified as electrodes specific to that organization.

19. The method of claim 5, wherein identifying the type of electrode pads further comprises identifying the number of magnets within the cable connector.

* * * * *